United States Patent [19]

Lindall et al.

[11] Patent Number: 4,508,828
[45] Date of Patent: Apr. 2, 1985

[54] BIOASSAY OF PARATHYROID HORMONE

[75] Inventors: Arnold W. Lindall, Marine-on-St. Croix; James J. Elting, North Oaks, both of Minn.

[73] Assignee: Immuno Nuclear Corporation, Stillwater, Minn.

[21] Appl. No.: 477,253

[22] Filed: Mar. 21, 1983

[51] Int. Cl.$^3$ ............... G01N 33/56; G01N 33/58; G01N 33/60
[52] U.S. Cl. ............................ 436/500; 422/61; 436/503; 436/504; 436/804; 436/808; 436/817; 436/824; 436/825
[58] Field of Search ............ 436/500, 503, 504, 804, 436/808, 817, 824, 825; 422/61

[56] References Cited

PUBLICATIONS

Bringhurst et al., *Biochem* 21: 4252–4258, (1982).
Zonefrati et al., *Acta Endocinologica* 100: 398–405, (1982).
Nissenson et al., *J. Clin. Endocrin. & Metab.* 52: 840–846, (1981).
Chambers et al., *Clin. Endocrinology* 9: 375–379, (1978).
Fenton et al., *Clin. Endocrinology* 9: 381–384, (1978).
Majeska et al., *Endocrinology* 107: 1494–1503, (1980).
Partridge et al., *Endocrinology* 108: 213–219, (1981).
Dunham et al., *Annals of the Rheumatic Disease* 41: 569–573, (1982).
Partridge et al., *Endocrinology* 108: 220–225, (1981).
Teitelbaum et al., *Endocrinology* 111: 1524–1533, (1982).
Nissenson et al., *Advances in Experimental Medicine and Biology* 151: 549–559, (1982).
Avioli et al., Abstracts: Mineral Metabolism; Pharmaceutical Hormone, *Calcified Tissue Int'l* 33: 318, (1981).

*Primary Examiner*—Christine M. Nucker
*Attorney, Agent, or Firm*—Dorsey & Whitney

[57] ABSTRACT

A method is disclosed for extraction, concentration, and bioassay measurement of the concentration of bioactive parathyroid peptides in biological or other fluids. Parathyroid peptides are extracted from the fluid by a support-antibody matrix specific to the N-terminal region. The bioassay is directed to the extracted parathyroid peptides. The volume of the medium containing the extracted parathyroid peptides and tissue, cells or tissue extracts with adenylate cyclase-coupled parathyroid hormone receptors may be chosen to be significantly less than the volume of biological or other fluid being assayed.

18 Claims, 5 Drawing Figures

BIOASSAY OF PARATHYROID HORMONE

BACKGROUND OF THE INVENTION

1. Field of the Invention

This invention involves the extraction, concentration and bioassay measurement of the concentration of parathyroid hormone in biological or other fluids. This application is related to U.S. Patent Application Ser. Nos. 442,649 filed Nov. 18, 1982 and 449,164 filed Dec. 13, 1982.

2. Description of the Prior Art

Human parathyroid hormone (hPTH) has a major role in maintaining the constancy (homeostasis) of calcium in cells and extracellular fluid, despite marked variations in calcium intake and excretion. It is now apparent that circulating PTH peptides fall into two groups: a common group and an unusual group. The common group consists of substantially intact hPTH believed to be hPTH$^{1-84}$ and fragments thereof believed to be hPTH$^{1-34}$ and hPTH$^{35-84}$. Of these, hPTH$^{1-84}$ and hPTH$^{1-34}$ are believed to be biologically active, while hPTH$^{35-84}$ is believed to be biologically inactive. Common group PTH peptides circulate in normal individuals and in those with primary and secondary hyperparathyroidism. The unusual group consists of a truncated form of substantially intact hPTH believed to be hPTH$^{1-64}$ and fragments thereof believed to be hPTH$^{1-34}$ and hPTH$^{35-64}$. Of these, hPTH$^{1-64}$ and hPTH$^{1-34}$ are believed to be biologically active, while hPTH$^{35-64}$ is believed to be biologically inactive. In parathyroid adenoma, tumors may secrete either or both groups, although clinical data indicates that secretion of the unusual group is quite common for this disorder.

There is increasing interest in measuring in human serum or plasma the concentration of the biologically active peptides of both the common group and the unusual group. Measurement of PTH in human serum or plasma by radioimmunoassay is well established, but, with the exception of the radioimmunoassay disclosed in U.S. Patent Application Ser. No. 449,164, such radioimmunoassays generally suffer from several disadvantages. One disadvantage is the difficulty of measuring the concentration of bioactive PTH in normal serum. The concentration of bioactive PTH in such cases is generally below the lower limit of the sensitivity of radioimmunoassays. Another disadvantage is that much of what is measured by radioimmunoassay is thought to be biologically inactive.

Sensitive and convenient bioassays for PTH, on the other hand, have not generally been available. Existing PTH bioassays utilize cultured animal tissue, cultured animal cells, or tissue extract containing adenylate cyclase-coupled PTH receptors. Certain PTH peptides bind the PTH receptors causing a complex response in the tissue, cells or extract which may be measured by the stimulated generation of cAMP. It can also be measured by the stimulation of glucose 6-phosphate dehydrogenase activity in the distal convoluted tubules of segments of kidney tissue maintained in vitro. Other means for measuring the stimulation of such PTH receptors are certainly possible in light of the complex response to such stimulation in the tissues, cells or extracts.

Bioassays directed to the stimulated generation of cAMP include the following. In F. Bringhurst, et al., "Metabolism Of Parathyroid Hormone By Kupffer Cells: Analysis By Reverse-Phase HPLC, "*BIOCHEM,* 21: 4252–4258 (1982), R. Zonefrati, et al., "Parathyroid Hormone Bioassay Using Human Kidney Cortical Cells In Primary Culture, "*ACTA ENDOCRINOLOGICA,* 100: 398–405 (1982), and R. Nissenson, et al., "Endogenous Biologically Active Human Parathyroid Hormone: Measurement By A Guanyl Nucleotide-Amplified Renal Adenylate Cyclase Assay," *J. CLIN. ENDOCRIN. & METAB.,* 52: 840–846 (1981), all incorporated in their entirety herein by reference thereto, the adenylate cyclase activity of, respectively, cultured cells of rat osteogenic sarcoma, cultured cells of normal human kidney cortical plasma membranes, and homogenized extracts of canine renal cortical plasma membranes are measured by cAMP generation. These bioassays illustrate prior art attempts to overcome a basic problem in measuring adenylate cyclase activity by cAMP. The concentration of bioactive hPTH in serum is generally below the sentivity of such bioassays. This is especially so for serum taken from normal subjects, but is also pronounced for serum taken from renal dialysis patients where the concentration of bioactive PTH is only slightly elevated from undetectably low normal values.

The bioassay disclosed in Zonefrati, supra, illustrates the search for a more sensitive assay in the choice of tissue containing the adenylate cyclase activity. The bioassay disclosed in Bringhurst, supra, illustrates the search for a more sensitive assay in the choice of tissue and in using radioimmunoassay of cAMP. The bioassay disclosed in Nissenson, supra, illustrates the search for a more sensitive assay in amplifying adenylate cyclase activity and cAMP generation by incorporating Gpp(NH)p. These prior art attempts at increasing the sensitivity of bioassays measuring adenylate cyclase activity by cAMP generation are not wholly satisfactory, however, as evidenced by the lower limits of sensitivity claimed for these bioassays.

Bioassays measuring stimulation of glucose 6-phosphate dehydrogenase activity in the distal convoluted tubules of segments of kidneys are commonly referred to as "cytochemical bioassays." Cytochemical bioassays are believed to utilize the same receptor as the above discussed assays but measure stimulation of glucose 6-phosphate dehydrogenase activity rather than adenylate cyclase activity. Examples of such bioassays are disclosed in D. Chambers, et al., "A Sensitive Bioassay Of Parathyroid Hormone In Plasma," *CLIN. ENDOCRINOLOGY,* 9: 375–379 (1978) and S. Fenton, et al., "Preliminary Studies With The Sensitive Cytochemical Assay For Parathyroid Hormone," *CLIN. ENDOCRINOLOGY,* 9: 381–384 (1978). These cytochemical bioassays have respective sensitivities of 5 fg/ml and 0.1 fg/ml of bioactive PTH in serum samples. The sensitivity of these cytochemical bioassays reaches far below the concentration of bioactive PTH in normal serum. These cytochemical bioassays, however, suffer from a very serious disadvantage. As pointed out in Nissenson, supra, at p. 844, although the cytochemical bioassays are capable of detecting femptogram quantities of bioactive PTH in serum, these elegant bioassays are not practical for the routine assay of PTH in large numbers of samples. The cytochemical bioassay requires a remarkably high level of experimental and laboratory expertise of its practitioners. The cytochemical bioassay also requires a substantial amount of time and effort in performing the assay.

Measuring bioactive PTH peptides in human serum can prove to be an extremely helpful and effecient clinical tool in the differential diagnosis and management of hypercalcemia; most notably, it can help to diagnose tumors and hyperplasia of parathyroid glands. Measuring bioactive PTH peptides in human serum can also be useful for the diagnosis and management of hypocalcemia, which is usually reflected as subnoral blood concentratios of bioactive PTH peptides. PTH bioassay can also be used to assess the status of renal osteodystrophy in renal failure patients on chronic dialysis. The application of PTH bioassay in differential diagnosis and management of these disease states requires a bioassay with a sensitivity capable of measurements in the 10 picomole/liter range while also being capable of assaying large numbers of samples in a clinical setting. The prior art bioassays discussed above do not fulfill these requirements.

SUMMARY OF THE INVENTION

The invention relates generally to PTH bioassays which incorporate cultured animal tissue, cultured animal cells, or tissue extract containing adenylate cyclase-coupled PTH receptors. The invention is based on the discovery that the sensitivity of such bioassays is significantly increased by extracting biologically active PTH from serum or plasma prior to exposing the tissue, cells or tissue extract to the bioactive PTH. The invention is also based on the discovery that the extracted bioactive PTH peptides may be conveniently concentrated prior to exposing the tissue, cells or tissue extract to the peptides. Utilizing a concentrated extract in such bioassays will also significantly increase their sensitivity.

The invention comprises extracting from a measured volume of a biological or other fluid, with a support-antibody matrix specific to the N-terminal region, mammalian PTH peptides to which the matrix is specific. This step is followed by contacting the extracted mammalian PTH peptides with cultured animal tissue, cultured animal cells, or tissue extract containing adenylate cyclase-coupled PTH receptors in a measured volume of medium and under conditions suitable for the extracted mammalian PTH peptides to bind the PTH receptors. The concentration of bioactive mammalian PTH peptides in the original fluid is indicated by measuring the response to binding to the PTH receptors. This may be accomplished by measuring stimulation of adenylate cyclase coupled to PTH receptors. This stimulation of adenylate cyclase may be measured by cAMP generation. The binding to the PTH receptors may also be measured by stimulation of glucose 6-phosphate dehydrogenase activity. This bioassay may be directed generally against mammalian PTH peptides but should be especially suitable for bioassay of rat PTH peptides, bovine PTH peptides, porcine peptides, and hPTH peptides.

The mammalian PTH peptides may be extracted from the biological or other fluids, especially from serum or plasma, by a method which comprises (a) contacting a measured initial quantity of the fluid with a support-antibody matrix specific to the N-terminal region;

(b) allowing under suitable conditions reaction of the matrix antibodies with mammalian PTH peptides to which they are specific to proceed substantially to equilibrium;

(c) separating the support-antibody matrix and mammalian PTH peptides coupled thereto from the remaining fluid and uncoupled mammalian PTH peptides contained therein;

(d) contacting the separated support-antibody matrix and mammalian PTH peptides coupled thereto with a decoupling solution under suitable conditions for decoupling the mammalian PTH peptides coupled to the support-antibody matrix;

(e) allowing under suitable conditions substantial decoupling of the mammalian PTH peptides coupled to the support-antibody matrix; and (f) separating the remaining solution and decoupled mammalian PTH peptides contained therein from the support-antibody matrix.

The fluid and support-antibody matrix may be contacted per step (a) by adding the fluid and support-antibody matrix into an affinity chromatography column. The matrix antibodies may be allowed to react substantially to equilibrium with mammalian PTH peptides to which they are specific per step (b) by maintaining contact of the matrix with the peptides in the column under suitable conditions until the reaction substantially reaches equilibrium. The support-antibody matrix and mammalian PTH peptides coupled thereto may be separated from the remaining fluid and uncoupled mammalian PTH peptides contained therein per step (c) by allowing the remaining fluid and uncoupled peptides to drain through the column. The support-antibody matrix and mammalian PTH peptide coupled thereto may be contacted with the decoupling solution per step (d) by adding the decoupling solution to the column containing the matrix and coupled peptides. The mammalian PTH peptides coupled to the support-antibody matrix may be allowed to substantially decouple per step (e) by maintaining contact of the decoupling solution and the matrix in the column until such substantial decoupling. The remaining solution and decoupled mammalian PTH peptides contained therein may be separated from the support-antibody matrix per step (f) by allowing the remaining solution and peptides contained therein to drain through the column.

The mammalian PTH peptides contained in the remaining solution per step (f) may be separated from the remaining solution by lyophilizing the remaining solution containing the extracted mammalian PTH peptides. The product of the lyophilization may be reconstituted by the medium or a constituent of the medium in which the tissue, cells, or tissue extracts are contacted with the extracted PTH peptides. The concentration of the extracted PTH peptides in the medium may be significantly increased relative to their concentration in the fluid by maintaining the total volume of medium at a value substantially less than the volume of the fluid.

The extraction of bioactive PTH peptides is useful in bioassays where the animal tissue, cells or tissue extract contain adenylate cyclase-coupled PTH receptors. By extracting bioactive PTH peptides from serum or plasma prior to contacting such peptides with the adenylate cyclase-coupled PTH receptors, nonspecific interference by the serum or plasma is eliminated. Such nonspecific interference by serum or plasma is attributable in part to the presence of non-PTH hormones and peptides present in the serum or plasma which can stimulate adenylate cyclase activity and/or activate the generation of cAMP.

The extraction procedure eliminates the need to add serum or plasma stripped of PTH to known standards in an attempt to compensate for nonspecific interference in the unknown sample. Although stripped plasma or serum has been added to known standards in the cytochemical bioassay where the assay is extremely sensitive (cf. Chambers, supra, at p. 377), the addition of stripped serum or plasma to known standards in the case of bioassays directed to cAMP is inappropriate. As shown below, serum or plasma significantly suppresses cAMP generation and will exascerbate the lack of sensitivity already plaguing such bioassays.

A further advantage is available by concentrating the extracted bioactive PTH peptides prior to exposing the peptides to the tissue, cells or tissue extracts containing the adenylate cyclase-coupled PTH receptors. The volume of the medium, in which the tissue, cells or tissue extracts are exposed to the extracted peptides, is essentially a matter of choice. By chosing a volume for the medium which is significantly less than the volume of the unknown serum or plasma sample, the sensitivity of the bioassay will be correspondingly significantly increased. A five-fold reduction of serum sample volume to medium volume, for example, will result in a five-fold increase in sensitivity of the assay.

DESCRIPTION OF THE PREFERRED EMBODIMENT

The following is a description of a typical preparation and operation of a PTH bioassay incorporating a support-antibody matrix specific to the N-terminal region for extracting bioactive PTH peptides from biological or other fluids such as serum or plasma. The PTH bioassay also incorporates cultured animal tissue, cultured animal cells or tissue extract containing adenylate cyclase-coupled PTH receptors for measuring the stimulation of such PTH receptors by the extracted peptides. The following described PTH bioassay illustrates the concentration of extracted bioactive PTH peptides prior to exposing the tissue, cells or tissue extract to such extracted peptides.

1. Preparation Of Rat Osteogenic Sarcoma Cell Culture.

Rat osteogenic sarcoma cells are maintained in culture in Dulbecco's modified Eagle medium ("DMEM"), disclosed in R. Dulbecco, *VIROLOGY*, 8: 396 (1959), J. Smith, et al., *VIROLOGY*, 12: 185-196 (1960), Tissue Culture Standards Committee, *IN VITRO*, 6(2): 93 and available from Gibco, Grand Island, N.Y., containing 1% fetal calf serum, 9% heat-inactivated horse serum, 100 units/ml of penecilin G and 100 μg/ml streptomycin sulfate in sodium sulfate and normal saline solution, available as a concentrate from Gibco, supra. Cells are maintained in this medium in a humidified atmosphere of 5% carbon dioxide and 95% air at 37° C. This rat osteogenic sarcoma cell culture can be obtained according to the methods set forth in N. Partridge, et al., "Functional Properties Of Hormonally Responsive Cultured Normal And Malignant Rat Ostoblastic Cells," *ENDOCRINOLOGY*, 108: 213-219 (1981), which is incorporated in its entirety herein by reference thereto. This method of obtaining the cell culture is further described in R. Majeska, et al., "Parathyroid Hormone—Responsive Clonal Cell Lines From Rat Osteosarcoma," *ENDOCRINOLOGY*, 107: 1494-1503 (1980) and R. Majeska, "Maintenance Of Parathyroid Hormone Response in Clonal Rat Osteosarcoma Cell Lines," *EXP. CELL RES.*, 111: 465 (1978), also incorporated in their entirety herein by reference thereto.

Cells are subcultured from confluent monolayers by removing the culture medium, rinsing the cell layer with Dulbecco's phosphate buffered saline, 0.2 g/l KCl, 0.2 g/l $KH_2PO_4$, 4.0 g/l NaCl, and $Na_2HPO_4.7H_2O$ and available from Gibco, supra, and adding trypsin/EDTA, 0.5 g trypsin (1:250) and 0.2 g EDTA-4Na/l Hank's balanced salt solution without $CaCl_2$, $MGCL_2.6H_2O$ and $MgSO_4.7H_2O$ and available from Gibco, supra, to cover the cell layer. After 1 minute at 20°-25° C., the trypsin/EDTA is removed and the cells are incubated for 2-3 minutes at 37° C. The cells are resuspended in DMEM and one-fifth to one-tenth of the cells are added to a culture flask of equal size.

For use in the bioassay of PTH, the above cell suspension is diluted with 4 volumes of DMEM and 0.1 ml of the suspension is pipetted into each well of a 96-well tissue culture plate available from Becton Dickinson Labware, Oxnard, Calif. The cells are cultured in the same atmosphere as above and are ready for use in the bioassay in 24-28 hours.

2. Extraction And Concentration Of PTH Peptides.

A support-antibody matrix specific to the N-terminal region may be prepared by conjugating an antibody specific to that particular region to a water insoluble support.

The following method may be used to prepare a pool of chicken antibody specific to the N-terminal region at a concentration in 1% BSA-0.1M borate buffer which, according to its titer, will result in at least 40 to 60% binding. 10 mg of $hPTH^{1-34}$, available commercially from Peninsula Laboratories, Inc., Belmont, Calif. 94002, was conjugated by conventional means to 50 mg keyhole limpet hemocyanin with 2.5 mg ethyl carbodiimide. 0.5 mg of $hPTH^{1-34}$, as conjugated, is injected into a chicken with weekly boosters of 0.25 mg of $hPTH^{1-34}$ as conjugated. In about the fifth week, chickens are bled from a vein under the wing and tested for good titer.

Plasma isolated from a chicken's blood by centrifugation is titered using $^{125}I$-$hPTH^{1-34}$. Dilutions of 1/500, 1/1000, 1/3000, 1/5000, and 1/10,000 by volume are prepared by adding to the isolated chicken plasma appropriate quantities of 1% BSA-0.1M borate buffer (pH 8.4). 50 μl of Zero Standard (defined infra), and 200 μl of each dilution of chicken plasma are combined and incubated for four hours at 2°-8° C. 200 μl of $^{125}I$-$hPTH^{1-34}$ Reagent (defined infra) is added to the incubation mixture. After vortexing gently and incubating for 16-20 hours at 2°-8° C., the N-terminal region RIA protocol (defined infra) is followed, beginning with the addition of RAC-PPT Reagent. Percent binding of the chicken antibody to $^{125}I$-$hPTH^{1-34}$ against dilution of the chicken plasma is plotted according to the counts registered for precipitated and non-precipitated $^{125}I$-$hPTH^{1-34}$. Good titer is represented by dilution which has at least 40-60% binding. The animal is bled biweekly if good titer is present. The animal may be maintained by injecting 0.25 mg of $hPTH^{1-34}$ as conjugated.

An antibody from a chicken was found which has a high affinity constant. It reacts with the N-terminal region but not with the mid-region or C-terminal region. This antibody has a very high affinity for bovine and human peptides containing the N-terminal region. This antibody also has a substantially high affinity for rat PTH peptides containing the N-terminal region. It is thought that this antibody will have a substantially high affinity for the parathyroid hormone of any mammal and any fragments containing the N-terminal region.

Antibodies specific to the N-terminal region may be conjugated to a solid support as follows. A pool of chicken antibody with desired specificity is purified with saturated ammonium sulfate. Equal volumes of pooled chicken plasma and saturated ammonium sulfate are added and gently stirred for 12 hours at 4° C. This mixture is centrifuged at 14,000 rpm for 30 minutes at 4° C. using a Beckman J2-21 centrifuge and a JA-14 rotor (available commercially from Beckman Instruments, Inc., Fullerton, Calif. 92631). After discarding the supernatant, the precipitate is dissolved in distilled water and dialized at 4° C. against 0.85% wgt./vol. saline-distilled water solution using three changes.

The ammonium sulfate purified antibody may be conjugated to agarose and cross-linked dextran activated by carbonyldiimidazole (which is available commercially as Reacti-Gel, Pierce Chemical Co., Rockford, Ill. 61105 and disclosed in Bethell, et al., "A Novel Method of Activation of Cross-Linked Agaroses with 1,1-Carbonyldiimidazole Which Gives A Matrix for Affinity Chromatography Devoid of Additional Charged Groups," *J. of Biol. Chem.*, Vol. 254, pp. 2572-2574 (1979), which is incorporated herein by reference). 12.5 ml of purified antibody is added to 30 ml of packed Reacti-Gel and approximately 100 ml of coupling buffer (0.1M sodium bicarbonate and 0.5M sodium chloride in distilled water, pH 8.0). This mixture is rotated overnight at 4° C.

In the alternative, agarose activated with cyanogen bromide, available commercially as Sepharose from Pharmacia, Inc., Piscatawa, N.J. 08854 may be used as the support. 12.5 ml of purified antibody are mixed with 15 g of activated and swelled Sepharose and 100 ml of coupling buffer. This mixture is rotated 12 hours at 4° C.

The rotated Reacti-Gel mixture, or in the alternative the rotated Sepharose mixture, is centrifuged for 7 minutes at 2000 rpm in a refrigerated centrifuge. Fines and supernate are carefully aspirated off. The remaining material is washed two times with 200 ml of coupling buffer, followed by centrifugation and aspiration of fines and supernate. 50 ml of 0.2M glycine-0.1M borate buffer (pH 8.0) are added to the remaining material. This is followed by rotation at room temperature for 1 hour and centrifugation for 7 minutes at 2000 rpm in a refrigerated centrifuge. After the supernate is aspirated off, the matrix is washed with approximately 200 ml of 0.2M acetate buffer (pH 4.0), centrifuged for 7 minutes at 2000 rpm in a refrigerated centrifuge with supernate aspirated off. The matrix is then washed with 200 ml 0.1M borate-1.0M NaCl (ph 8.0) centrifuged for 7 minutes at 2000 rpm in a refrigerated centrifuge with the supernate aspirated off. The preceding two washes are repeated two more times. The matrix is then washed two times with 200 ml of 1.0% BSA-0.1M borate, centrifuged for 7 minutes at 2000 rpm in a refrigerated centrifuge with supernate aspirated off. 25 ml of 1.0% BSA-0.1M borate are added to the matrix and the mixture is allowed to settle overnight in a refrigerator. The matrix is diluted to five times the settled volume in 1.0% BSA-0.1M borate. The binding capacity of the support-antibody matrix is determined by incubating 0.5 ml of this diluted matrix with High Standard (defined infra) for two hours at room temperature under rotation. After centrifugation, the supernate should be devoid of PTH peptides to which the conjugated antibody was specific. This can be determined by assaying the supernate with a double antibody immunoassay where the first antibody has the same specificity as the conjugated antibody. 6.25 ml of the matrix at 1:2.5 dilution are placed in a vial and lypholized at 2°-8° C. This may be reconstituted with 25 ml of distilled water to form Support-Antibody Matrix Reagent.

As further alternatives, other supports may be utilized to form the matrix. Such supports are discussed in U.S. Pat. No. 3,720,760, issued Mar. 13, 1973, U.S. Pat. No. 3,645,853, issued Feb. 29, 1972, and the Bethell, et al., article supra, all of which are incorporated herein by reference. Also as alternative embodiments, antibodies specific to the N-terminal region may be raised in animals other than chickens. Also antibodies may be raised in chickens or such other animals against substances other than those particular substances which are disclosed herein or in the references to have been injected in the animals.

Bioactive PTH peptides may be extracted from a biological or other fluid such as serum or plasma and concentrated by use of a support-antibody matrix specific to the N-terminal region as follows:

1. Affinity chromatography columns (95×6 mm with a frit of 35 micron pore size, available commercially from Evergreen Scientific, Catalogue No. 208-3368-050) are placed upright in a rack.
2. 1.0 ml of well-mixed suspended Support-Antibody Matrix Reagent specific to the N-terminal region is added to each column.
3. Each column is washed with three 1 ml aliquots of 0.85% saline, allowed to drain, and the bottom of the columns are capped.
4. 2-5 ml of serum are added to each column.
5. The top of each column is capped.
6. The columns are rotated (the contents mixed end over end) for two hours at 20°-25° C. Rotors are available commercially from Markson Science Supplies, Catalogue No. 256-990 or Scientific Industries Ames, Catalogue No. R4190.
7. The columns are placed in a rack and both top and bottom caps are removed thereby allowing the plasma to drain through the columns.
8. A rubber bulb is used to force remaining plasma through the columns.
9. Each column is washed with three 1 ml aliquots of 0.85% saline and allowed to drain.
10. Remaining saline is forced from the columns using a rubber bulb.
11. Coupled PTH peptides are eluted by adding to each column 250 µl of 0.025N HCl and after one minute forcing the decoupling solution through the column using a rubber bulb.
12. The preceding step 11 is repeated.
13. The combined eluates from steps 11 and 12 are frozen at −80° C.
14. The frozen eluates are lyophilized.
15. The dried eluates are dissolved in 0.6 ml of bioassay medium at 20°-25° C., said bioassay medium consisting of 0.1% glucose, 1% BSA, 1 mM methylisobutylxanthine, and 0.005% phenol red in Dulbecco's phosphate buffer saline (pH 7.3 or within range of about 7-7.5).

3. Bioassay of PTH Peptides.

To perform the bioassay of PTH, the medium is removed from all wells of the 96-well tissue culture plate containing the rat osteogenic sarcoma cells by inversion of the plate and blotting of any remaining drops of medium. The plate is replaced upright and 100 µl of the redissolved N-terminal affinity column eluates are added to each of 4 wells of the plate. The plate is incubated at 20°-25° C. for 30 minutes. At this time, the plate is inverted and blotted to remove all remaining medium, replaced upright and placed on ice.

Each well is washed 3 times by addition of 300 µl of ice cold 0.85% saline followed by inversion and blocking. After the third saline wash, 200 µl of ice cold 95% ethyl alcohol containing 0.02M HCl (EtOH/HCl) is added to each well and the plate is incubated at −20° C. for 16-24 hours in order to extract the cAMP from the cells. At the end of this extraction, the EtOH/HCl is removed from each well with a pipet and rinsed with an additional 200 µl of EtOH/HCl. The rinse is combined with the original extract and the solution is dried. An appropriate device for drying the EtOH/HCl samples is a Speed-Vac Concentrator/Evaporator, available from Savant Instruments, Inc., Hicksville, N.Y. The amount of cAMP extracted from the cell layer in each well is quantitated using a radioimmunoassay for cAMP.

A standard solution of $bPTH^{1-84}$ is prepared by dissolving $bPTH^{1-84}$ in bioassay medium at a concentration of 10 µg/ml. A standard solution containing 10 ng/ml is then prepared by dilutions of 10 µl of the 10 µg/ml solution with 990 µl of bioassay medium and further diluting 100 µl of this solution with 900 µl of bioassay medium. Doubling dilutions of this stock are made containing 5,000, 2,500, 1,250, 625, 312, 161, 80.5, 40.2 and 20.1 pg/ml by dilution with bioassay medium. 100 µl of each standard is added to each of 4 wells of the plate to generate a standard curve from which PTH concentration is calculated after assay for cAMP.

4. Radioimmunoassay Of cAMP.

$^{125}$I-cAMP is prepared by dissolving 2.5 µg of (0-2)-monosuccinyl-adenosine 3':5'-cyclic monophosphate tyrosyl methyl ester (cAMP-TME), available from Sigma Chemical Company, St. Louis, Mo., in 1 ml of 505 ethyl alcohol. 0.1 ml of this stock is diluted in glass distilled water to give a new stock containing 0.1 µg of cAMP-TME per ml. 25 µl of stock containing 2.5 µg of cAMP-TME is mixed with 20 µl of 0.5M Na phosphate buffer (pH 7.4). ≅µl of 0.05M Na phosphate buffer (pH 7.4) containing 50 µg of chloramine T, available from Sigma Chemical Company, supra, is added, and the solution is thoroughly mixed. After 60 seconds, 75 µl of 0.05M Na phosphate buffer (pH 7.4) containing 180 µg of Na metabisulfite, available from Sigma Chemical Company, supra, is added and the solution is thoroughly mixed. The reaction mixture is applied to a 30×1 cm chromatographic column packed with Sephadex G-25, available from Pharmacia Fine Chemicals, Piscataway, N.J., and is equilibrated with 0.2M Na acetate buffer (pH 5.8) containing 2 mg/ml of bovine serum albumin (BSA), available from IN VITRO Research Sources, Benson, Md., sold as a 30% solution containing 0.1% Na azide. The reaction vial is rinsed with 200 µl of the Na acetate/BSA solution and added to the top of the chromatographic column. The top of the column is connected to a buffer reservoir containing Na acetate/BSA and 1.0 ml aliquots are collected from the outlet of the column. Fractions were then collected, pooled, and diluted for use in radioimmunoassay.

50 mM Na acetate buffer containing 15 mM calcium chloride (pH 6.2)("Na acetate buffer") is prepared. A stock solution of adenosine 3':5'-cyclic monophosphate, available from Sigma Chemical Company, supra, is made by dissolving 2.81 mg of cAMP in 100 ml of Na acetate buffer. The stock solution is serially diluted with Na acetate buffer to form standards containing 80, 40, 20, 10, 5 and 2.5 picomoles/ml.

Rabbit anti-cAMP serum may be prepared according to the methods set forth in W. Schrader and B. O'Malley (editors), LAB METHODS MANUAL FOR HORMONE ACTION AND MOLECULAR ENDOCRINONOLGY (5th ED.), Chapter 9. The rabbit anti-cAMP serum obtained according to the above method is diluted to a concentration at which there is 50-70% binding of $^{125}$I-cAMP in 3 hours at 20-25 C. using 0.1M Na borate (pH 8.2-8.4) containing 0.1% BSA.

Goat anti-rabbit Ig pre-precipitated second antibody may be prepared according to the method set forth in U.S. patent application Ser. No. 442,649 filed Nov. 18, 1982, which is incorporated in its entirety herein by reference thereto.

Radioimmunoassay of cAMP may be performed as follows:
1. Duplicate Disposable 12×75 mm glass tubes, available from Scientific Products, Div. of American Hospital Supply Corp., McGraw Park, Ill., are set up and identified for the following protocol.
2. Add reagents as follows:
   a. Nonspecific binding tubes—250 µl of Na acetate buffer.
   b. Zero standard—50 µl of Na acetate buffer—200 µl of rabbit anti-cAMP serum.
   c. cAMP standards (2.5-80 pmoles/ml)—50 µl of cAMP standard. 200 µl of rabbit anti-cAMP serum.
   d. Serum unknown—50 µl of product of incubation of cell culture and reconstituted and concentrated extract. 200 µl of rabbit anti-cAMP serum.
   e. $bPTH^{1-84}$ standards—50 µl of product of incubation of cell culture and $bPTH^{1-84}$ standards. 200 µl of rabbit anti-cAMP serum.
3. Add 200 µl of $^{125}$I-cAMP to all tubes.
4. Mix and incubate for 3 hours ±15 minutes at 20°-25° C.
5. Add 500 µl of goat anti-rabbit IGg pre-precipitated second antibody.
6. Mix and incubate for 15±5 minutes at 20°-25° C.
7. Centrifuge for 20 minutes at a minimum of 2500 RPM at 20°-25° C.
8. Decant supernatant into a 12×75 mm disposable glass test tube.
9. In a gamma scintillation counter, count the precipitate and supernatant from each tube.

The concentration of bioactive PTH peptides in the unknown human serum may be determined by reference to a standard curve. Standard curves may be obtained by several methods, for example by plotting percent binding vs. concentration of $bPTH^{1-84}$ standard or by plotting cpm of precipitate, or the supernatant, or the ratio therebetween vs. concentration of the $bPTH^{1-84}$ standard. The cAMP standards may be utilized to prepare a standard curve by plotting percent binding vs. concentration of cAMP in order to confirm proper performance of the cAMP radioimmunoassay. The percent binding may be calculated by the formula:

$$\text{percent binding} = \frac{cpm \text{ sample precipitate}}{cpm \text{ sample precipitate} + cpm \text{ sample supernatant}}$$

As an alternative embodiment, the results of the nonspecific binding (NSB) sample may be incorporated in the calculation of the percent binding. NSB is the result of radioactive supernatant residing in the precipitate and protein binding to the walls of the assay tubes as well as other factors.

5. Results of the PTH Bioassay.

Figure 1:
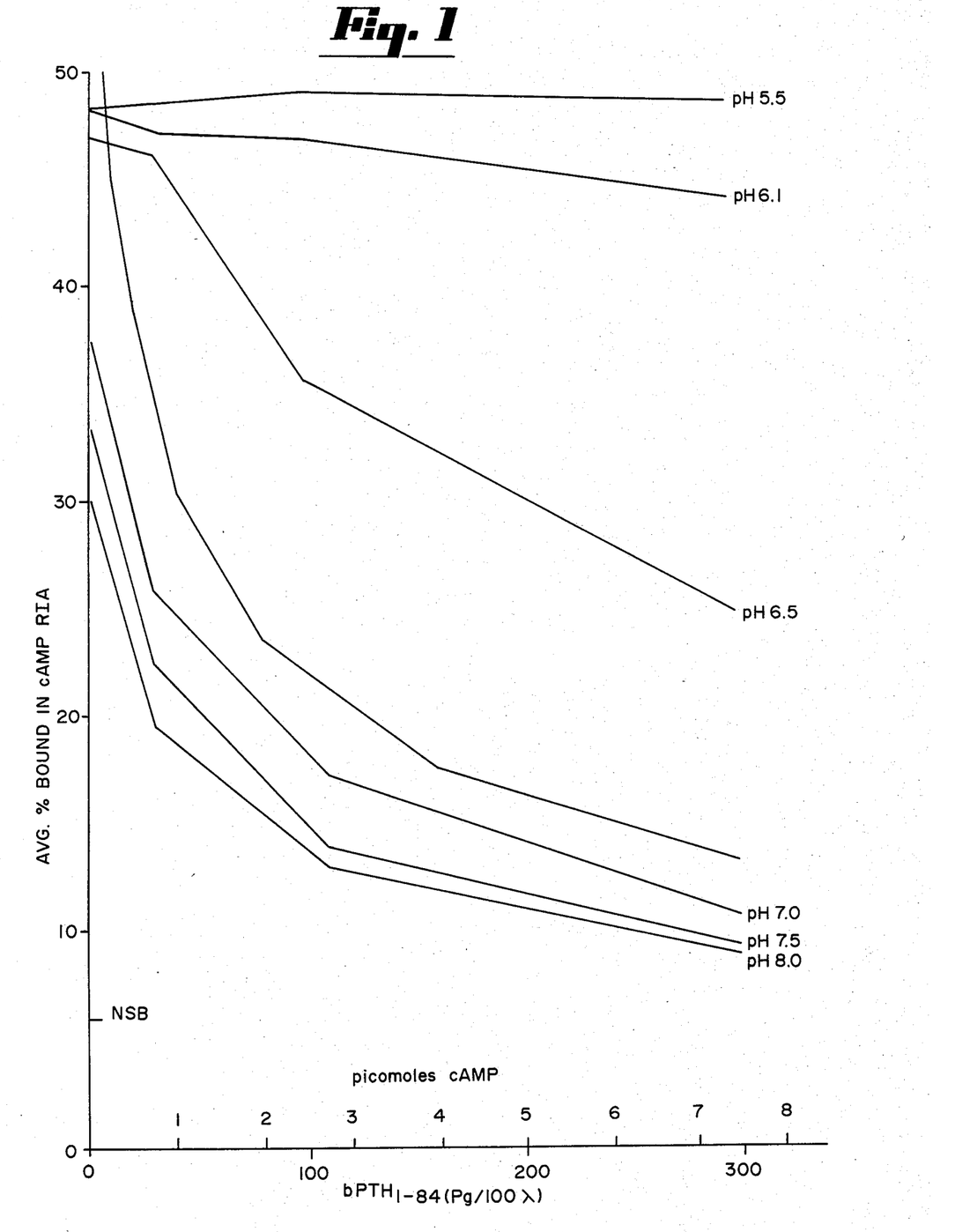
FIG. 1 shows the effect of the pH of the medium to generation of cAMP by $hPTH^{1-84}$.

In the preferred embodiment, lyophilized eluates containing extracted PTH from unknown serum and bPTH$^{1-84}$ standards are reconstituted with buffered bioassay medium. Lyophilizing will remove most of the HCl used to decouple the extracted PTH peptides from the support-antibody matrix. 0.1M NaOH or 0.1M HCl may be added to the reconstituted extract in bioassay media to bring the pH of the medium within an optimal range of about 7–7.5. This optimal range was determined by incubating the cell culture and bPTH$^{1-84}$ standards in bioassay media of varying pH as shown in FIG. 1.

Figure 2:
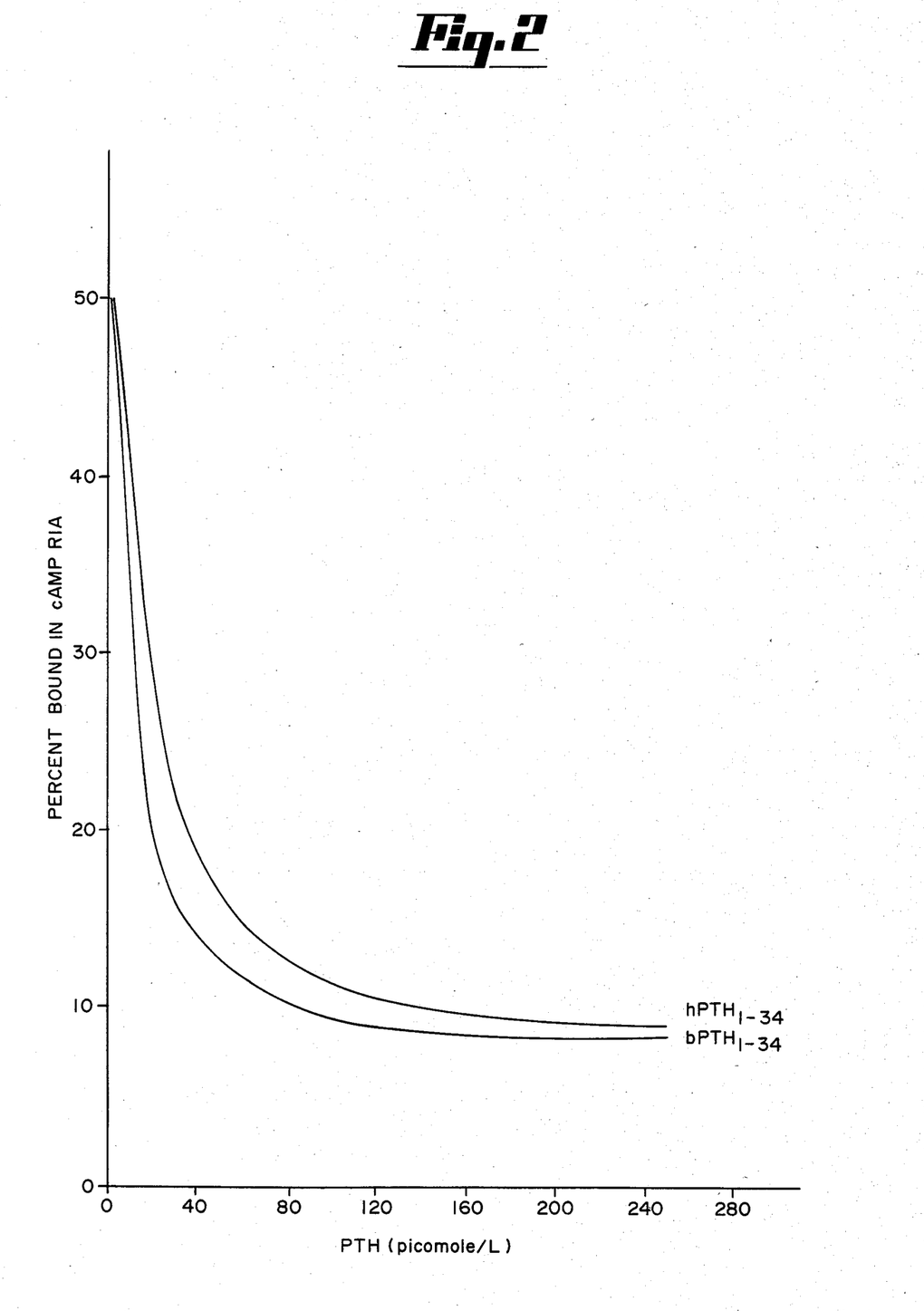
FIG. 2 shows that rat osteogenic sarcoma cells respond similarly to $bPTH^{1-34}$ and $hPTH^{1-34}$.

The preferred bioassay utilizes bPTH$^{1-84}$ as a standard for assaying hPTH. Accordingly, a comparison was made of rat osteogenic sarcoma cell culture response to human and bovine bioactive PTH. FIG. 2 shows a very close correlation of response to hPTH$^{1-34}$ and bPTH$^{1-34}$, thereby validating the use of bovine PTH standard to bioassay human serum.

Figure 3:
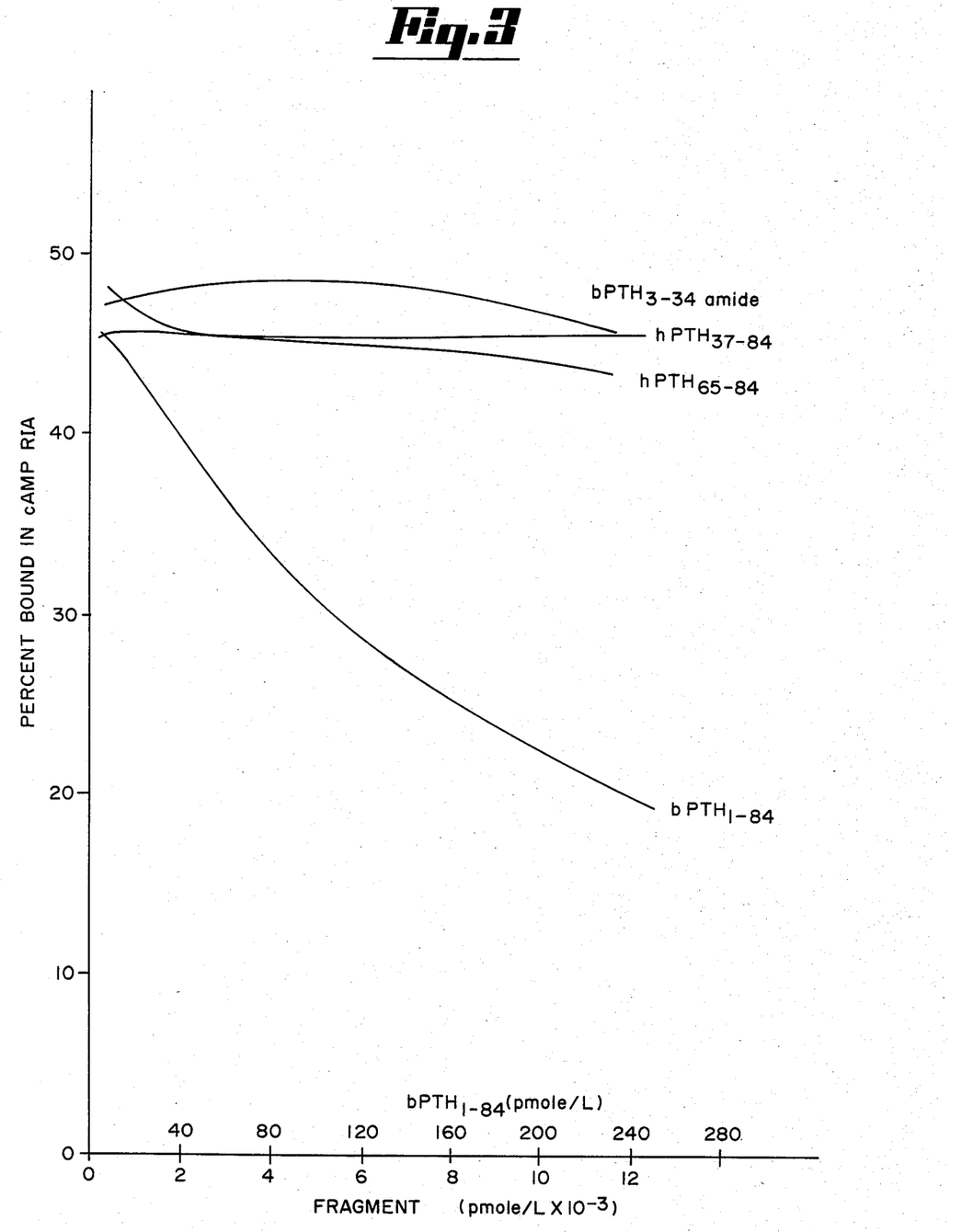
FIG. 3 shows that $hPTH^{3-34}$ amide, $hPTH^{37-84}$, and $hPTH^{65-84}$ are not bioactive.
Figure 4:
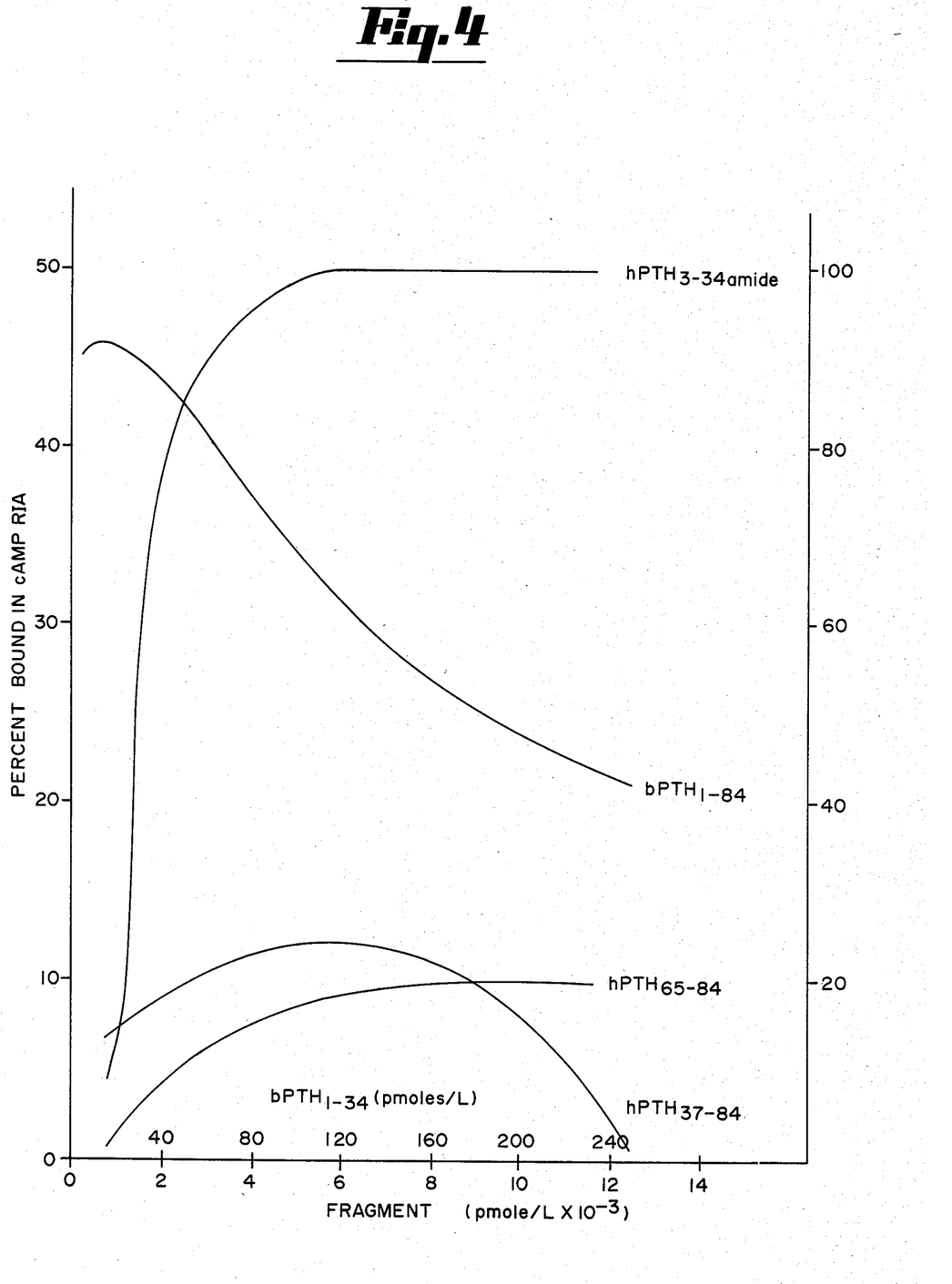
FIG. 4 shows the inhibition of cAMP generation by $hPTH^{3-34}$ amide, $hPTH^{37-84}$, and $hPTH^{65-84}$.

In order to show that the above PTH bioassay measures the concentration in serum of bioactive PTH peptides and not biologically inactive PTH peptides, the bioassay was performed on standards containing (norleucine$^{8,18}$)bPTH$^{3-34}$amide (hereinafter "bPTH$^{3-34}$amide") hPTH$^{37-84}$ and hPTH$^{65-84}$. The bioassay was again performed on the preceding standards after bPTH$^{1-84}$ had been added to the standards. The bioassay indicated a virtual absence of bioactivity for bPTH$^{3-34}$amide, hPTH$^{37-84}$ and hPTH$^{65-84}$ as shown in FIG. 3. bPTH$^{3-34}$amide is shown in FIG. 4 to be a very strong antagonist of bPTH$^{1-84}$, which confirms that the above bioassay is specific to bioactive PTH peptides and not biologically inactive PTH peptides or other non-PTH peptides.

Figure 5:
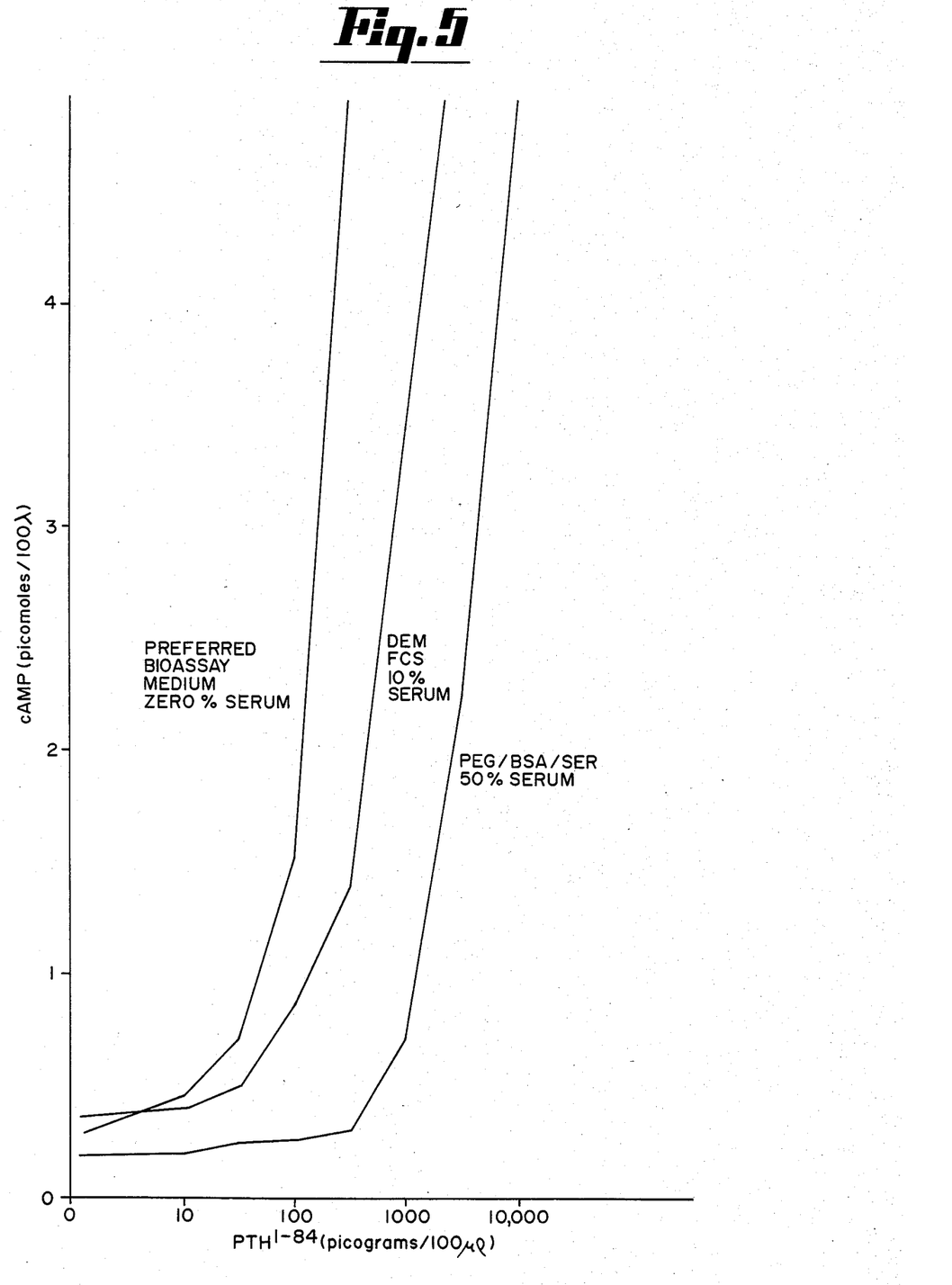
FIG. 5 shows the inhibition of cAMP generation by serum.

In order to demonstrate that serum present in the bioassay medium will suppress cAMP generation by as much as 100-fold, the above bioassay was performed on PTH$^{1-84}$ standards. In the first set of assays, the bioassay medium consisted of the preferred embodiment bioassay medium disclosed above. In the second set of assays, the bioassay medium consisted of DEM containing 1.0 mM preferred embodiment bioassay medium and 10% fetal calf serum. In the third set of bioassays, the bioassay medium consisted of a mixture of the preferred embodiment bioassay medium and 50% human serum (T$_3$, T$_4$, cortisol deficient serum, available commercially from Ventrex Labs, Portland, Maine). FIG. 5 shows a 50-fold and 100-fold suppression of cAMP generation due respectively to 10% serum and 50% serum content in the bioassay medium. This serves to illustrate the advantage of the extraction procedure whereby PTH peptides are exposed to PTH receptors in a serum-free environment.

6. Alternative Embodiments.

As alternatives to the foregoing bioassay, the animal tissue culture, animal cell culture or tissue extract may be bound to a support to form a support-tissue, support-cell or support-tissue extract matrix. Also, the tissue culture, cell culture, tissue extract, support-tissue matrix, support-cell matrix or support-tissue extract matrix may be converted to respectively a tissue preparation, cell preparation or tissue extract preparation which may be reconstituted or reactivated for use in the bioassay. In the case of support matrices, the support may comprise agarose and cross linked dextran activated by carbonyldiinidazol or agarose activated with cyanogen bromide.

The extraction and concentration procedure set forth above may be used to enhance the sensitivity of bioassays other than the above preferred bioassay which utilizes rat osteogenic sarcoma cell culture. The above extraction and concentration procedure will enhance the sensitivity of the bioassays disclosed in Bringhurst, Zonefrati, Nissenson, Chambers and Fenton, all supra. Thus, the extraction and concentration procedure may be used to enhance bioassays incorporating such diverse materials as rat osteogenic sarcoma cell cultures, canine renal plasma membranes, human kidney cortical cell culture and other cultured animal tissue, cultured animal cells or tissue extract containing adenylate cyclase-coupled PTH receptors.

From the foregoing it will be obvious to those skilled in the art that various modifications in the above described methods and articles of manufacture can be made without departing from the spirit and scope of the invention. Accordingly, the invention may be embodied in other specific forms without departing from the spirit or essential characteristics thereof. Present embodiments, therefore, are to be considered in all respects as illustrative and not restrictive, the scope of the invention being indicated by the appended claims rather than by the foregoing descriptions, and all changes which come within the meaning and range of equivalency of the claims are therefore intended to be embraced therein.

We claim:

1. A method of bioassay of mammalian parathyroid peptides in biological or other fluids comprising:
   extracting from a measured volume of the biological or other fluid, with a support-antibody matrix specific to the N-terminal region of mammalian parathyroid hormone, mammalian parathyroid peptides to which the matrix is specific;
   contacting the extracted mammalian parathyroid peptides with cultured animal tissue, cultured animal cells, or tissue extract containing adenylate cyclase-coupled parathyroid hormone receptors in a measured volume of medium and under conditions suitable for the extracted mammalian parathyroid peptides to bind the parathyroid hormone receptors; and
   measuring the response to binding of the parathyroid hormone receptors.

2. The method of claim 1 wherein the mammalian parathyroid peptides are members of the group consisting of rat parathyroid peptides, bovine parathyroid peptides, porcine parathyroid peptides, and human parathyroid peptides.

3. The method of claim 2 wherein said members are human parathyroid peptides.

4. The method of claim 3 wherein said biological or other fluid is human serum or plasma.

5. The method of claim 1 wherein the support-antibody matrix comprises the antibody coupled to agarose and cross linked dextran activated by carbonlydiimidazole or the antibody coupled to agarose activated with cyanogen bromide.

6. The method of claim 1 wherein the extraction from the fluid of the mammalian parathyroid peptides to which the matrix is specific further comprises
   (a) contacting the measured quantity of the fluid with the support-antibody matrix specific to the N-terminal region of mammalian parathyroid hormone;
   (b) allowing under suitable conditions reaction of the matrix antibodies with mammalian parathyroid peptides to which they are specific to proceed substantially to equilibrium;
   (c) separating the support-antibody matrix and mammalian parathyroid peptides coupled thereto from the remaining fluid and uncoupled mammalian parathyroid peptides contained therein;
   (d) contacting the separated support-antibody matrix and mammalian parathyroid peptides coupled thereto with a decoupling solution under suitable conditions for decoupling the mammalian parathyroid peptides coupled to the support-antibody matrix;
   (e) allowing under suitable conditions substantial decoupling of the mammalian parathyroid peptides coupled to the support-antibody matrix; and
   (f) separating the remaining solution and mammalian parathyroid peptides contained therein from the support-antibody matrix.

7. The method of claim 6 wherein
   the fluid and support-antibody matrix are contacted per step (a) by adding the fluid and support-antibody matrix into an affinity chromatography column;
   the matrix antibodies are allowed to react substantially to equilibrium with mammalian parathyroid peptides to which they are specific per step (b) by maintaining contact of the matrix with the peptides in the column under suitable conditions until the reaction substantially reaches equilibrium;
   the support-antibody matrix and mammalian parathyroid peptides coupled thereto are separated from the remaining fluid and uncoupled mammalian parathyroid peptides contained therein per step (c) by allowing the remaining fluid and uncoupled peptides to drain through the column;
   the support antibody matrix and mammalian parathyroid peptide coupled thereto are contacted with the decoupling solution per step (d) by adding the decoupling solution to the column containing said matrix and coupled peptides;
   the mammalian parathyroid peptides coupled to the support-antibody matrix are allowed to substantially decouple per step (e) by maintaining contact of the decoupling solution and the matrix in the column until such substantial decoupling; and
   the remaining solution and mammalian parathyroid peptides contained therein are separated from the support-antibody matrix per step (f) by allowing the remaining solution and peptides contained therein to drain through the column.

8. The method of claim 6 wherein the mammalian parathyroid peptides contained in the remaining solution per step (f) are separated from the remaining solution.

9. The method of claim 8 wherein the mammalian parathyroid peptides contained in the remaining solution per step (f) are separated from the remaining solution by lyophilizing the remaining solution containing the mammalian parathyroid peptides.

10. The method of claim 9 wherein the product of lyophilization is reconstituted by the medium or a constituent of the medium.

11. The method of claim 1 wherein the volume of the medium is substantially less than the volume of the biological or other fluid.

12. The method of claim 1 wherein the cultured animal cells are an osteogenic sarcoma cell culture.

13. The method of claim 12 wherein the binding of the parathyroid hormone receptors is measured by assaying stimulated cAMP generation by the osteogenic sarcoma cell culture.

14. The method of claim 1 wherein the tissue extract is canine renal cortical plasma membranes.

15. As an article of manufacture, an extraction-bioassay kit comprising at least one vial containing a support-antibody matrix specific to the N-terminal region of mammalian parathyroid hormone and at least one vial containing an animal tissue preparation, animal cell preparation, or tissue extract preparation which may be reconstituted, reactivated, or used respectively as cultured animal tissue, cultured animal cells, or tissue extract containing adenylate cyclase-coupled parathyroid hormone receptors.

16. The extraction-bioassay kit of claim 15 wherein the support of the support-antibody matrix comprises agarose and cross linked dextran activated by carbonyldiimidazole or agarose activated with cyanogen bromide.

17. The extraction-bioassay kit of claim 15 wherein the N-terminal region of mammalian parathyroid hormone is a member of the group consisting of the N-terminal region of rat parathyroid hormone, N-terminal region of bovine parathyroid hormone, N-terminal region of bovine parathyroid hormone, N-terminal region of porcine parathyroid hormone, and N-terminal region of human parathyroid hormone.

18. The extraction-bioassay kit of claim 17 wherein said member is the N-terminal region of human parathyroid hormone.

* * * * *